United States Patent
Gaffney et al.

(10) Patent No.: US 6,914,150 B2
(45) Date of Patent: Jul. 5, 2005

(54) MIXED-METAL OXIDE CATALYSTS AND PROCESSES FOR PREPARING THE SAME

(75) Inventors: Anne Mae Gaffney, West Chester, PA (US); Ruozhi Song, Wilmington, DE (US)

(73) Assignee: Rohm and Haas Company, Philadelphia, PA (US)

( * ) Notice: Subject to any disclaimer, the term of this patent is extended or adjusted under 35 U.S.C. 154(b) by 68 days.

(21) Appl. No.: 10/636,184

(22) Filed: Aug. 7, 2003

(65) Prior Publication Data

US 2004/0044248 A1 Mar. 4, 2004

Related U.S. Application Data

(62) Division of application No. 10/150,217, filed on May 17, 2002, now Pat. No. 6,642,174.
(60) Provisional application No. 60/292,996, filed on May 23, 2001.

(51) Int. Cl.[7] .......................... C07C 253/00; B01J 23/00
(52) U.S. Cl. ........................ 558/319; 502/311; 564/542
(58) Field of Search .......................... 502/311; 558/519; 564/542

(56) References Cited

U.S. PATENT DOCUMENTS

| 5,281,745 A | 1/1994 | Ushikubo et al. |
| 5,380,933 A | 1/1995 | Ushikubo et al. |
| 5,907,052 A | 5/1999 | Hamada et al. |

FOREIGN PATENT DOCUMENTS

| EP | 0962253 A | 8/1999 |
| JP | 7-53448 | 2/1995 |
| JP | 2000143244 A | 5/2000 |
| WO | WO0198246 | 12/2001 |

OTHER PUBLICATIONS

M. Campanati, et al., "Fundamentals in the Preparation of heterogeneous catalysts", Catalysis Today 77, Elsevier Science, Amesterdam, NL (2003) 299–314.

Watanabe, et al. "New Synthesis Route for MO–V–NB–TE Mixed Oxides Catalyst for Propane Ammoxidation", Applied Catalysis A: General, Elsevier Science, Amesterdam, NL, vol. 194–195, (Mar. 13, 2000), pp. 479–485, XP004272252.

Ueda, et al., "Hydrothermal Synthesis of MO–V–M–O Complex Metal Oxide Catalysts Active for Partial Oxidation of Ethane", Chemical Communications, Royal Society of Chemistry, GB, 1999, pp. 517–518, XP002229941.

Derwent Abstract XP002229942.

Translation of Japanese Laid Open Patent Application Publication No. 6–228073 (Aug. 16, 1994).

*Primary Examiner*—Kamal Saeed
(74) *Attorney, Agent, or Firm*—Allen Holler; Mareella M. Bodner

(57) ABSTRACT

An improved catalyst comprising a mixed metal oxide is prepared by the use of a sol-gel technique. The catalyst is useful for the conversion of an alkane, or a mixture of an alkane and an alkene, to an unsaturated carboxylic acid by vapor phase oxidation, or to an unsaturated nitrile by vapor phase oxidation in the presence of ammonia.

2 Claims, No Drawings

MIXED-METAL OXIDE CATALYSTS AND PROCESSES FOR PREPARING THE SAME

CROSS REFERENCE TO THE PATENT APPLICATIONS

This non-provisional application is a divisional of non-provisional U.S. patent application Ser. No. 10/150,217, filed May 17, 2002, now U.S. Pat. No. 6,642,174 benefit of which is claimed under 35 U.S.C. § 120 and which in turn claims benefit under 35 U.S.C. § 119(e) of U.S. Provisional Application No. 60/292,996, filed May 23, 2001, priority benefit of which is also claimed for the present divisional application.

This invention relates to processes for preparing mixed-metal oxide catalysts. More particularly, the present invention relates to processes for preparing mixed metal oxide catalysts that can be useful, for example, in the conversion of alkanes, or mixtures of alkanes and alkenes, to unsaturated carboxylic acids or unsaturated nitriles. Mixed-metal oxide catalysts with improved performance qualities are also disclosed.

Nitriles, such as acrylonitrile and methacrylonitrile, have been industrially produced as important intermediates for the preparation of fibers, synthetic resins, synthetic rubbers, and the like. The most popular method for producing such nitriles is to subject an olefin such as propene or isobutene to a gas phase catalytic reaction with ammonia and oxygen in the presence of a catalyst at a high temperature. Known catalysts for conducting this reaction include a Mo—Bi—P—O catalyst, a V—Sb—O catalyst, an Sb—U—V—Ni—O catalyst, a Sb—Sn—O catalyst, a V—Sb—W—P—O catalyst and a catalyst obtained by mechanically mixing a V—Sb—W—O oxide and a Bi—Ce—Mo—W—O oxide. However, in view of the price difference between propane and propene or between isobutane and isobutene, attention has been drawn to the development of a method for producing acrylonitrile or methacrylonitrile by an ammoxidation reaction wherein a lower alkane, such as propane or isobutane, is used as a starting material, and it is catalytically reacted with ammonia and oxygen in a gaseous phase in the presence of a catalyst.

In particular, U.S. Pat. No. 5,281,745 discloses a method for producing an unsaturated nitrile comprising subjecting an alkane and ammonia in the gaseous state to catalytic oxidation in the presence of a catalyst which satisfies the conditions:

(1) the mixed metal oxide catalyst is represented by the empirical formula $$Mo_a V_b Te_c X_x O_n$$

wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron and cerium and, when a=1, b=0.01 to 1.0, c=0.01 to 1.0, x=0.01 to 1.0 and n is a number such that the total valency of the metal elements is satisfied; and (2) the catalyst has X-ray diffraction peaks at the following angles (±0.3°) of 2θ in its X-ray diffraction pattern: 22.1°, 28.2°, 36.2°, 45.2° and 50.0°.

Similarly, Japanese Laid-Open Patent Application Publication No. 6-228073 discloses a method of nitrile preparation comprising reacting an alkane in a gas phase contact reaction with ammonia in the presence of a mixed metal oxide catalyst of the formula $$W_a V_b Te_c X_x O_n$$

wherein X represents one or more elements selected from niobium, tantalum, titanium, aluminum, zirconium, chromium, manganese, iron, ruthenium, cobalt, rhodium, nickel, palladium, platinum, antimony, bismuth, indium and cerium and, when a=1, b=0.01 to 1.0, c=0.01 to 1.0, x=0.01 to 1.0 and n is determined by the oxide form of the elements.

Unsaturated carboxylic acids such as acrylic acid and methacrylic acid are industrially important as starting materials for various synthetic resins, coating materials and plasticizers. Commercially, the current process for acrylic acid manufacture involves a two-step catalytic oxidation reaction starting with a propene feed. In the first stage, propene is converted to acrolein over a modified bismuth molybdate catalyst. In the second stage, acrolein product from the first stage is converted to acrylic acid using a catalyst composed of mainly molybdenum and vanadium oxides. In most cases, the catalyst formulations are proprietary to the catalyst supplier, but, the technology is well established. Moreover, there is an incentive to develop a single step process to prepare the unsaturated acid from its corresponding alkene. Therefore, the prior art describes cases where complex metal oxide catalysts are utilized for the preparation of unsaturated acid from a corresponding alkene in a single step.

Japanese Laid-Open Patent Application Publication No. 07-053448 discloses the manufacture of acrylic acid by the gas-phase catalytic oxidation of propene in the presence of mixed metal oxides containing Mo, V, Te, O and X wherein X is at least one of Nb, Ta, W, Ti, Al, Zr, Cr, Mn, Fe, Ru, Co, Rh, Ni, Pd, Pt, Sb, Bi, B, In, Li, Na, K, Rb, Cs and Ce.

Commercial incentives also exist for producing acrylic acid using a lower cost propane feed. Therefore, the prior art describes cases wherein a mixed metal oxide catalyst is used to convert propane to acrylic acid in one step.

U.S. Pat. No. 5,380,933 discloses a method for producing an unsaturated carboxylic acid comprising subjecting an alkane to a vapor phase catalytic oxidation reaction in the presence of a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium; and wherein the proportions of the respective essential components, based on the total amount of the essential components, exclusive of oxygen, satisfy the following relationships: 0.25<r(Mo)<0.98, 0.003<r(V)<0.5, 0.003<r(Te)<0.5 and 0.003<r(X)<0.5, wherein r(Mo), r(V), r(Te) and r(X) are the molar fractions of Mo, V, Te and X, respectively, based on the total amount of the essential components exclusive of oxygen.

Nonetheless, the prior art continues to seek ways to improve the performance of such mixed metal oxide catalysts.

The present invention is directed, in part, to an improved method for the preparation of catalysts. Specifically, in one embodiment, there is provided a process for the preparation of an improved catalyst comprising a mixed-metal oxide having the empirical formula $$Mo_a V_b E_c X_d O_e$$

wherein E is at least one element selected from the group consisting of Te and Sb, wherein X is at least one element selected from the group consisting of Nb, Ta, Ti, Al, Zr, Cr, Mn, Fe, Ru, Co, Rh, Ni, Pd, Pt, Ag, B, In, Ce and W, and wherein, when a=1, b=0.01 to 1.0, c=0.01 to 1.0, d=0.01 to 1.0 and e is dependent on the oxidation state of the other elements, said process comprising:

(a) admixing compounds of Mo, V, E and X and at least one solvent to form a gel;

(b) aging said so-formed gel; and (c) calcining said gel.

In another embodiment, there are provided catalysts, produced according to the foregoing method, having improved performance qualities.

In yet another embodiment, the present invention provides a process for the preparation of an unsaturated carboxylic acid.

In a still further embodiment, the present invention provides a process for the preparation on an unsaturated nitrile.

These and other aspects of the invention will become more apparent from the following detailed description.

In accordance with a typical embodiment, the present invention provides improved methods for the preparation of mixed metal oxide catalysts. The catalysts prepared according to the present methods can be advantageously employed in various processes, particularly in processes for the oxidation of alkanes, or mixtures of alkanes and alkenes, to their corresponding unsaturated carboxylic acids and unsaturated nitriles.

The methods of the present invention involve a sol-gel technique. As used herein, the term "sol-gel technique" refers to a material that is obtained through the formation of a colloidal dispersion or "sol" by hydrolysis and polycondensation, which upon further hydrolytic linking and continued condensation of the colloidal dispersion results in the formation of an interconnected, rigid network, or "gel".

A wide variety of metal oxides and/or metal salts can undergo such a sol-gel process as used in the methods of the present invention. Included among the metal salts that can be employed are, for example, metal halides and metal nitrates. Oxides and/or salts of metals which can be employed in the present methods include, for example, oxides and/or salts of metals such as, for example, molybdenum (Mo), vanadium (V), tellurium (Te), antimony (Sb), niobium (Nb), tantalum (Ta), titanium (Ti), aluminum (Al), zirconium (Zr), chromium (Cr), manganese (Mn), iron (Fe), ruthenium (Ru), cobalt (Co), rhodium (Rh), nickel (Ni), palladium (Pd), platinum (Pt), silver (Ag), boron (B), indium (In), cerium (Ce), tungsten (W), and mixtures thereof. Preferred metals include, for example, Mo, V, Te and Nb. Other metals, in addition to those exemplified above, would be readily apparent to one of ordinary skill in the art, once armed with the present disclosure.

Certain salts and/or oxides of molybdenum which can be employed in the present methods include, for example ammonium heptamolybdate (($NH_4$)$_6$$Mo_7$$O_{24}$), molybdenum oxides (such as, for example, $MoO_3$ and $MoO_2$), molybdenum chloride ($MoCl_5$), molybdenum oxychloride ($MoOCl_4$), $Mo(OC_2H_5)_5$, molybdenum acetylacetonate ($CH_3COCH=COCH_3$)$_3$Mo, phosphomolybdic acid ($MoO_3 \cdot H_3PO_4$) and silicomolybdic acid ($H_4SiO_4 \cdot MoO_3$). Generally, salts and/or oxides of vanadium which can be employed in the present methods include, for example, ammonium metavanadate ($NH_4VO_3$), vanadium oxides (such as, for example, $V_2O_5$, and $V_2O_3$), vanadium oxytrichloride ($VOCl_3$), vanadium chloride ($VCl_4$), vanadium oxytriethoxide ($VO(OC_2H_5)_3$), vanadium acetylacetonate ($CH_3COCH=COCH_3$)$_3$V and vanadyl acetylacetonate ($CH_3COCH=COCH_3$)$_2$VO. In some embodiments, salts and/or oxides of tellurium which can be employed in the present methods include, for example, telluric acid (Te(OH)$_6$), tellurium tetrachloride ($TeCl_4$), tellurium ethoxide (Te($OC_2H_5$)$_5$), tellurium isopropoxide (Te[$OCH(CH_3)_2$]$_4$), and tellurium dioxide ($TeO_2$). Typical salts and/or oxides of niobium which can be employed in the present methods include, for example, ammonium niobium oxalate, niobium oxide ($Nb_2O_5$), niobium chloride ($NbCl_5$), niobic acid, niobium ethoxide ($Nb(OC_2H_5)_5$) and niobium oxalate. Other oxides and salts of metals, in addition to those exemplified above, would be readily apparent to one of ordinary skill in the art, once armed with the present disclosure.

As noted above, the aforementioned oxides and/or salts of metals are employed in the present methods in the forms of a sol and then a gel. A wide variety of solvents can be employed in connection with the sol-gel technique. Typical among the solvents useful in the sol-gel preparation are polar solvents. More typically polar solvents include, for example, water, alcohols including, for example, alkanols, such as methanol, ethanol and propanol, and diols, such as glycols, including ethylene glycol and propylene glycol. Most typical among these solvents is water. The particular form of water employed can vary, and is generally any water suitable for use in chemical synthesis including, for example, distilled water and de-ionized water. Other solvents, in addition to those exemplified above, would be readily apparent to one of ordinary skill in the art, once armed with the present disclosure.

The amount of solvent employed in the preparation can vary and depends, for example, on the particular metal salts and/or oxides employed, the particular solvent employed, and the like. Generally speaking, the solvent is employed in an amount sufficient to place the salts and/or oxides substantially in solution, thereby avoiding or minimizing compositional and/or phase segregation. The term "substantially", as used herein in connection with solutions of metal salts and/or oxides, means that generally at least 70% of the salt and/or oxide goes into solution. More generally, the solvent is employed in an amount such that at least 80% of the salt and/or oxide goes into solution, preferably at least 90% being in solution. Most preferably, the solvent is employed in an amount such that the salts and/or oxides go completely into solution (i.e., 100% of the salt and/or oxide remains in solution).

Once the gel has formed, it is aged, i.e. it is allowed to stand in a quiescent state for from 1 hour to several weeks, e.g., 3 weeks, preferably, for from 4 hours to 100 hours, more preferably, from 6 to 60 hours. (Gel formation is indicated by the ability of the sol to support a stress elastically, this is referred to as the gelation point, a sharp increase in viscosity accompanies gelation. Aging is measured from the occurrence of this gelation point.) While it is possible to allow the gel to age for longer periods of time than set forth above, no significant further improvement in catalyst performance is expected. Typically, the aging is effected at room temperature, although higher and/or lower temperatures are permissible. In regard to temperature, the temperature should be above the freezing point of the solvent or mixture of solvents utilized and below the boiling point (at atmospheric pressure) of the solvent or mixture of solvents utilized. Depending upon the conditions prevailing during the aging process, some or all of the solvent or mixture of solvents may evaporate during the course of the aging step.

After the gel has been aged, residual solvent may be removed prior to calcination of the gel to provide a substantially dry gel. Techniques which would be suitable for removing solvent to provide the dried gel mixture would be readily apparent to one skilled in the art, once armed with the teachings of the present disclosure. Typical methods include, for example, vacuum drying, freeze drying, spray drying, rotary evaporation, and/or air drying. Vacuum drying can generally be performed at pressures ranging, for example, from 10 to 500 mm/Hg, and all combinations and subcombinations of ranges and specific pressures therein. Freeze drying can typically entail freezing the gel using, for example, liquid nitrogen, and drying the frozen material under vacuum. Spray drying can generally be performed under an inert atmosphere such as nitrogen or argon, with an inlet temperature ranging from 125° C. to 200° C. (and all combinations and subcombinations of ranges and specific temperatures therein) and an outlet temperature ranging from 75° C. to 150° C. (and all combinations and subcombinations of ranges and specific temperatures therein). Rotary evaporation can generally be performed at a bath temperature ranging, for example, from 25° C. to 90° C., and all combinations and subcombinations of ranges and specific temperatures therein. Generally, rotary evaporation can be performed using bath temperatures of from 40° C. to 90° C., with bath temperatures of from 40° C. to 60° C. in some embodiments. Rotary evaporation can also generally be performed at a pressure of from 10 mm/Hg to 760 mm/Hg, and all combinations and subcombinations of ranges and specific pressures therein. Specifically, rotary evaporation can be performed at a pressure of from 10 mm/Hg to 350 mm/Hg, with pressures of from 10 mm/Hg to 40 mm/Hg being other embodiments. Air drying can be conducted, for example, at temperatures ranging from 25° C. to 90° C., and all combinations and subcombinations of ranges and specific temperatures therein. In certain forms, the gel mixture is substantially dried by using rotary evaporation or air drying.

In accordance with the method of the present invention, the gel or the substantially dried gel is subjected to calcination. Calcination may be conducted in an oxidizing atmosphere, e.g., in air, oxygen-enriched air or oxygen, or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 hr$^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired promoted mixed metal oxide.

In a preferred mode of operation, calcination is conducted in two stages. In the first stage, the catalyst precursor is calcined in an oxidizing environment (e.g. air) at a temperature of from 200° C. to 400° C., preferably from 275° C to 325° C, for from 15 minutes to 8 preferably for from 1 to 3 hours. In the second stage, the material from the first stage is calcined in a non-oxidizing environment (e.g., an inert atmosphere) at a temperature of from 500° C. to 750° C., preferably for from 550° C. to 650° C., for from 15 minutes to 48 hours, preferably for from 1 to 24 hours, most preferably for from 2 to 10 hours. Optionally, a reducing gas, such as, for example, ammonia or hydrogen, may be added during the second stage calcination.

In a particularly preferred mode of operation, in the first stage, the material to be calcined is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

The calcination can be carried out in any suitable heating device, such as, for example, a furnace. Generally speaking, any type of furnace can be utilized during the heating steps. In certain embodiments of the present invention, the heating steps can be conducted under a flow of the involved gas environment. In such embodiments, the heating can be conducted in a bed with continuous flow of the gas through the bed of solid catalyst particles.

In accordance with this invention, calcining the gel material for a suitable time and at a suitable temperature desirably affords a catalyst comprising a mixed-metal oxide. The catalysts produced by the typical methods of this invention exhibit improved performance properties over the prior art. In more typical forms, the catalysts of this invention exhibit higher selectivity and yield when used in the oxidation of propane to produce acrylic acid. In a more typical form, the mixed-metal oxide catalysts have the formula

$$Mo_aV_bE_cX_dO_e$$

wherein when a is 1;

b is 0.01 to 1.0;

c is 0.01 to 1.0;

d is 0.01 to 1.0;

e is determined by the oxidation state of the cations present;

E is at least one element selected from the group consisting of Te and Sb; and

X is at least one element selected from the group consisting of Nb, Ta, Ti, Al, Zr, Cr, Mn, Fe, Ru, Co, Rh, Ni, Pd, Pt, Ag, Sb, Bi, B, In, Ce and W.

Preferably, when a=1, b=0.1 to 0.5, c=0.05 to 0.5 and d=0.01 to 0.5. More preferably, when a=1, b=0.15 to 0.45, c=0.05 to 0.45 and d=0.01 to 0.1. The value of e, i.e. the amount of oxygen present, is dependent on the oxidation state of the other elements in the catalyst. However, e is typically in the range of from 3 to 4.7.

The catalysts prepared using the methods of the present invention can be employed in various processes, particularly in processes for the oxidation of alkanes, or mixtures of alkanes and alkenes, to their corresponding unsaturated carboxylic acids. In another form, the present catalysts can be used in the ammoxidation of alkanes, or mixtures of alkanes and alkenes, to their corresponding unsaturated nitrites.

In the production of such an unsaturated carboxylic acid, it is preferred to employ a starting material gas which contains steam. In such a case, as a starting material gas to be supplied to the reaction system, a gas mixture comprising a steam-containing alkane, or a steam-containing mixture of alkane and alkene, and an oxygen-containing gas, is usually used. However, the steam-containing alkane, or the steam-containing mixture of alkane and alkene, and the oxygen-containing gas may be alternately supplied to the reaction system. The steam to be employed may be present in the form of steam gas in the reaction system, and the manner of its introduction is not particularly limited.

Further, as a diluting gas, an inert gas such as nitrogen, argon or helium may be supplied. The molar ratio (alkane or mixture of alkane and alkene): (oxygen): (diluting gas): ($H_2O$) in the starting material gas is preferably (1):(0.1 to 10):(0 to 20):(0.2 to 70), more preferably (1):(1 to 5.0):(0 to 10):(5 to 40).

When steam is supplied together with the alkane, or the mixture of alkane and alkene, as starting material gas, the selectivity for an unsaturated carboxylic acid is distinctly improved, and the unsaturated carboxylic acid can be obtained from the alkane, or mixture of alkane and alkene, in good yield simply by contacting in one stage. However, the conventional technique utilizes a diluting gas such as nitrogen, argon or helium for the purpose of diluting the starting material. As such a diluting gas, to adjust the space velocity, the oxygen partial pressure and the steam partial pressure, an inert gas such as nitrogen, argon or helium may be used together with the steam.

As the starting material alkane it is preferred to employ a $C_{3-8}$alkane, particularly propane, isobutane or n-butane; more preferably, propane or isobutane; most preferably, propane. According to the present invention, from such an alkane, an unsaturated carboxylic acid such as an $\alpha,\beta$-unsaturated carboxylic acid can be obtained in good yield. For example, when propane or isobutane is used as the starting material alkane, acrylic acid or methacrylic acid will be obtained, respectively, in good yield.

In the present invention, as the starting material mixture of alkane and alkene, it is possible to employ a mixture of $C_{3-8}$alkane and $C_{3-8}$alkene, particularly propane and propene, isobutane and isobutene or n-butane and n-butene. As the starting material mixture of alkane and alkene, propane and propene or isobutane and isobutene are more preferred. Most preferred is a mixture of propane and propene. According to the present invention, from such a mixture of an alkane and an alkene, an unsaturated carboxylic acid such as an $\alpha,\beta$-unsaturated carboxylic acid can be obtained in good yield. For example, when propane and propene or isobutane and isobutene are used as the starting material mixture of alkane and alkene, acrylic acid or methacrylic acid will be obtained, respectively, in good yield. Preferably, in the mixture of alkane and alkene, the alkene is present in an amount of at least 0.5% by weight, more preferably at least 1.0% by weight to 95% by weight; most preferably, 3% by weight to 90% by weight.

As an alternative, an alkanol, such as isobutanol, which will dehydrate under the reaction conditions to form its corresponding alkene, i.e. isobutene, may also be used as a feed to the present process or in conjunction with the previously mentioned feed streams.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the oxidation reaction of the present invention is not clearly understood, but the oxidation reaction is carried out by oxygen atoms present in the above promoted mixed metal oxide or by molecular oxygen present in the feed gas. To incorporate molecular oxygen into the feed gas, such molecular oxygen may be pure oxygen gas. However, it is usually more economical to use an oxygen-containing gas such as air, since purity is not particularly required.

It is also possible to use only an alkane, or a mixture of alkane and alkene, substantially in the absence of molecular oxygen for the vapor phase catalytic reaction. In such a case, it is preferred to adopt a method wherein a part of the catalyst is appropriately withdrawn from the reaction zone from time to time, then sent to an oxidation regenerator, regenerated and then returned to the reaction zone for reuse. As the regeneration method of the catalyst, a method may, for example, be mentioned which comprises contacting an oxidative gas such as oxygen, air or nitrogen monoxide with the catalyst in the regenerator usually at a temperature of from 300° to 600° C.

These aspects of the present invention will be described in further detail with respect to a case where propane is used as the starting material alkane and air is used as the oxygen source. The reaction system may be a fixed bed system or a fluidized bed system. However, since the reaction is an exothermic reaction, a fluidized bed system may preferably be employed whereby it is easy to control the reaction temperature. The proportion of air to be supplied to the reaction system is important for the selectivity for the resulting acrylic acid, and it is usually at most 25 moles, preferably from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other alkanes such as isobutane, or to mixtures of alkanes and alkenes such as propane and propene, the composition of the feed gas may be selected in accordance with the conditions for propane.

Typical reaction conditions for the oxidation of propane or isobutane to acrylic acid or methacrylic acid may be utilized in the practice of the present invention. The process may be practiced in a single pass mode (only fresh feed is fed to the reactor) or in a recycle mode (at least a portion of the reactor effluent is returned to the reactor). General conditions for the process of the present invention are as follows: the reaction temperature can vary from 200° C. to 700° C., but is usually in the range of from 200° C. to 550° C., more preferably 250° C. to 480° C., most preferably 300° C. to 400° C.; the gas space velocity, SV, in the vapor phase reaction is usually within a range of from 100 to 10,000 $hr^{-1}$, preferably 300 to 6,000 $hr^{-1}$, more preferably 300 to 2,000 $hr^{-1}$; the average contact time with the catalyst can be from 0.01 to 10 seconds or more, but is usually in the range of from 0.1 to 10 seconds, preferably from 2 to 6 seconds; the pressure in the reaction zone usually ranges from 0 to 75 psig, but is preferably no more than 50 psig. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the reaction zone.

Of course, in the oxidation reaction of the present invention, it is important that the hydrocarbon and oxygen concentrations in the feed gases be maintained at the appropriate levels to minimize or avoid entering a flammable regime within the reaction zone or especially at the outlet of the reactor zone. Generally, it is preferred that the outlet oxygen levels be low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning becomes less of a problem which enables the attainment of higher selectivity to the desired products. The catalyst of the present invention operates more efficiently at the lower temperature range set forth above, significantly reducing the formation of acetic acid and carbon oxides, and increasing selectivity to acrylic acid. As a diluting gas to adjust the space velocity and the oxygen partial pressure, an inert gas such as nitrogen, argon or helium may be employed.

When the oxidation reaction of propane, and especially the oxidation reaction of propane and propene, is conducted by the method of the present invention, carbon monoxide, carbon dioxide, acetic acid, etc. may be produced as by-products, in addition to acrylic acid. Further, in the method of the present invention, an unsaturated aldehyde may sometimes be formed depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it again to the vapor phase catalytic oxidation with the promoted mixed metal oxide-containing catalyst of the present invention or by subjecting it to a vapor phase catalytic oxidation reaction with a conventional oxidation reaction catalyst for an unsaturated aldehyde.

In a further aspect, the present invention provides processes for producing an unsaturated nitrile, which comprises subjecting an alkane, or a mixture of an alkane and an alkene, to a vapor phase catalytic oxidation reaction with ammonia in the presence of a catalyst produced in accord with the present invention to produce an unsaturated nitrile.

In the production of such an unsaturated nitrile, as the starting material alkane, it is preferred to employ a $C_{3-8}$alkane such as propane, butane, isobutane, pentane, hexane and heptane. However, in view of the industrial application of nitrites to be produced, it is preferred to employ a lower alkane having 3 or 4 carbon atoms, particularly propane and isobutane.

Similarly, as the starting material mixture of alkane and alkene, it is possible to employ a mixture of $C_{3-8}$alkane and $C_{3-8}$alkene such as propane and propene, butane and butene, isobutane and isobutene, pentane and pentene, hexane and hexene, and heptane and heptene. However, in view of the industrial application of nitriles to be produced, it is more preferred to employ a mixture of a lower alkane having 3 or 4 carbon atoms and a lower alkene having 3 or 4 carbon atoms, particularly propane and propene or isobutane and isobutene. Preferably, in the mixture of alkane and alkene, the alkene is present in an amount of at least 0.5% by weight, more preferably at least 1.0% by weight to 95% by weight, most preferably 3% by weight to 90% by weight.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the ammoxidation reaction of this aspect of the present invention is not clearly understood. However, the oxidation reaction is conducted by the oxygen atoms present in the above promoted mixed metal oxide or by the molecular oxygen in the feed gas. When molecular oxygen is incorporated in the feed gas, the oxygen may be pure oxygen gas. However, since high purity is not required, it is usually economical to use an oxygen-containing gas such as air.

As the feed gas, it is possible to use a gas mixture comprising an alkane, or a mixture of an alkane and an alkene, ammonia and an oxygen-containing gas, However, a gas mixture comprising an alkane or a mixture of an alkane and an alkene and ammonia, and an oxygen-containing gas may be supplied alternately.

When the gas phase catalytic reaction is conducted using an alkane, or a mixture of an alkane and an alkene, and ammonia substantially free from molecular oxygen, as the feed gas, it is advisable to employ a method wherein a part of the catalyst is periodically withdrawn and sent to an oxidation regenerator for regeneration, and the regenerated catalyst is returned to the reaction zone. As a method for regenerating the catalyst, a method may be mentioned wherein an oxidizing gas such as oxygen, air or nitrogen monoxide is permitted to flow through the catalyst in the regenerator usually at a temperature of from 300° C. to 600° C.

These aspects of the present invention will be described in further detail with respect to a case where propane is used as the starting material alkane and air is used as the oxygen source. The proportion of air to be supplied for the reaction is important with respect to the selectivity for the resulting acrylonitrile. Namely, high selectivity for acrylonitrile is obtained when air is supplied within a range of at most 25 moles, particularly 1 to 15 moles, per mole of the propane. The proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propene, the composition of the feed gas may be selected in accordance with the conditions for propane.

The processes of these aspects of the present invention may be conducted at a temperature of, for example, from 250° C. to 480° C. More preferably, the temperature is from 300° C. to 400° C. The gas space velocity, SV, in the gas phase reaction is usually within the range of from 100 to 10,000 hr$^{-1}$, preferably from 300 to 6,000 hr$^{-1}$, more preferably from 300 to 2,000 hr$^{-1}$. As a diluent gas, for adjusting the space velocity and the oxygen partial pressure, an inert gas such as nitrogen, argon or helium can be employed. When ammoxidation of propane is conducted by the method of the present invention, in addition to acrylonitrile, carbon monoxide, carbon dioxide, acetonitrile, hydrocyanic acid and acrolein may form as by-products.

For purposes of this application "% conversion" is equal to (moles of consumed alkane/moles of supplied alkane)× 100; and "% yield" is equal to (moles of formed desired unsaturated carboxylic acid/moles of supplied alkane)× (carbon number of formed desired unsaturated carboxylic acid/ carbon number of the supplied alkane)×100.

EXAMPLE 1

100 mL of an aqueous solution containing ammonium heptamolybdate tetrahydrate (1.0M Mo), ammonium metavanadate (0.3M V) and telluric acid (0.23M Te), formed by dissolving the corresponding salts in water at 70° C., was added to a 1000 mL rotavap flask. Then 50 mL of an aqueous solution of niobium oxalate (0.25M Nb) and oxalic acid (0.31M) were added thereto. An orange colored gel was formed in 5 to 10 min. After removing the water via a rotary evaporator with a warm water bath at 50° C. and 28 mm/Hg, the solid materials were further dried in a vacuum oven at 25° C. overnight and then calcined. (Calcination was effected by placing the solid materials in an air atmosphere and then heating them to 275° C. at 10° C./minute and holding them under the air atmosphere at 275° C. for one hour; the atmosphere was then changed to argon and the material was heated from 275° C. to 600° C. at 2° C./minute and the material was held under the argon atmosphere at 600° C. for two hours.) The final catalyst had a nominal composition of $Mo_1V_{0.3}Te_{0.23}Nb_{0.125}O_x$. The catalyst, thus obtained, was pressed in a mold and then broken and sieved to 10–20 mesh granules for subsequent evaluation.

EXAMPLE 2

100 mL of an aqueous solution containing ammonium heptamolybdate tetrahydrate (1.0M Mo), ammonium metavanadate (0.3M V) and telluric acid (0.23M Te), formed by dissolving the corresponding salts in water at 70° C., was added to a 1000 mL polyvap flask. Then 50 mL of an aqueous solution of niobium oxalate (0.25M Nb) and oxalic acid (0.31M) were added thereto. An orange colored gel was formed in 5 to 10 minutes. The gel was aged for 48 hours. After removing the water via a polyvap evaporator with a warm water bath at 50° C. and 28 mm/Hg, the solid materials were further dried in a vacuum oven at 25° C. overnight. 34 grams of solid catalyst precursor were recovered. 17 grams of this solid precursor were calcined by placing the solid materials in an air atmosphere and then heating them to 275° C. at 10° C./minute and holding them under the air atmosphere at 275° C. for one hour; the atmosphere was then changed to argon and the material was heated from 275° C. to 600° C. at 2° C./minute and the material was held under the argon atmosphere at 600° C. for two hours. The final catalyst had a nominal composition of $Mo_1V_{0.3}Te_{0.23}Nb_{0.125}O_x$. The catalyst, thus obtained, was pressed in a mold and then broken and sieved to 10–20 mesh granules for reactor evaluation.

EXAMPLE 3

The other 17 grams of the solid precursor from Example 2 were calcined by placing the solid materials in an air atmosphere and then heating them to 275° C. at 10° C./minute and holding them under the air atmosphere at 275° C. for one hour; the atmosphere was then changed to argon and the material was heated from 275° C. to 600° C. at 2° C./minute and the material was held under the argon atmosphere at 600° C. for five hours. The final catalyst had a nominal composition of $Mo_1V_{0.3}Te_{0.23}Nb_{0.125}O_x$. The catalyst, thus obtained, was pressed in a mold and then broken and sieved to 10–20 mesh granules for reactor evaluation.

EXAMPLE 4

100 mL of an aqueous solution containing ammonium heptamolybdate tetrahydrate (1.0M Mo), ammonium metavanadate (0.3M V) and telluric acid (0.23M Te), formed by dissolving the corresponding salts in water at 70° C., was added to a 1000 mL polyvap flask. Then 50 mL of an aqueous solution of niobium oxalate (0.25M Nb) and oxalic acid (0.31M) were added thereto. An orange colored gel was formed in 5 to 10 minutes. The gel was aged for 48 hours. After removing the water via a polyvap evaporator with a warm water bath at 50° C. and 28 mm/Hg, the solid materials were further dried in a vacuum oven at 25° C. overnight. 34 grams of solid catalyst precursor were recovered. 17 grams of this solid precursor were calcined by placing the solid materials in an air atmosphere and then heating them to 275° C. at 1° C./minute and holding them under the air atmosphere at 275° C. for one hour; the atmosphere was then changed to argon and the material was heated from 275° C. to 600° C. at 2° C./minute and the material was held under the argon atmosphere at 600° C. for ten hours. The final catalyst had a nominal composition of $Mo_1V_{0.3}Te_{0.23}Nb_{0.125}O_x$. The catalyst, thus obtained, was pressed in a mold and then broken and sieved to 10–20 mesh granules for reactor evaluation.

EXAMPLE 5

The other 17 grams of the solid precursor from Example 4 were calcined by placing the solid materials in an air atmosphere and then heating them to 275° C. at 10° C./minute and holding them under the air atmosphere at 275° C. for one hour; the atmosphere was then changed to argon and the material was heated from 275° C. to 600° C. at 2° C./minute and the material was held under the argon atmosphere at 600° C. for fifteen hours. The final catalyst had a nominal composition of $Mo_1V_{0.3}Te_{0.23}Nb0.125O_x$. The catalyst, thus obtained, was pressed in a mold and then broken and sieved to 10–20 mesh granules for reactor evaluation.

EXAMPLE 6

100 mL of an aqueous solution containing ammonium heptamolybdate tetrahydrate (1.0M Mo), ammonium metavanadate (0.3M V) and telluric acid (0.23M Te), formed by dissolving the corresponding salts in water at 70° C., was added to a 500 mL beaker. Then 50 mL of an aqueous solution of niobium oxalate (0.25M Nb) and oxalic acid (0.31M) were added thereto. An orange colored gel was formed in 5 to 10 minutes. The gel was dried to under atmospheric pressure and ambient temperature for three weeks. A solid catalyst precursor was obtained and calcined by placing the solid materials in an air atmosphere and then heating them to 275° C. at 10° C./minute and holding them under the air atmosphere at 275° C. for one hour; the atmosphere was then changed to argon and the material was heated from 275° C. to 600° C. at 2° C./minute and the material was held under the argon atmosphere at 600° C. for two hours. The final catalyst had a nominal composition of $Mo_1V_{0.3}Te_{0.23}Nb_{0.125}O_x$. The catalyst, thus obtained, was pressed in a mold and then broken and sieved to 10–20 mesh granules for reactor evaluation.

Evaluation and Results

Catalysts were evaluated in a 10 cm long Pyrex® tube reactor (internal diameter: 3.9 mm). The catalyst bed (4 cm long) was positioned with glass wool at approximately mid-length in the reactor and was heated with an electric furnace. Mass flow controllers and meters regulated the gas flow rate. The oxidation was conducted using a feed gas stream of propane, steam and air, with a feed ratio of propane:steam:air of 1:3:96. The reactor effluent was analyzed by an FTIR. The results (along with reaction temperature and residence time) are shown in Table 1.

TABLE 1

| Example | Temperature (° C.) | Residence Time (sec) | Propane Conversion (%) | Acrylic Acid Yield (%) |
|---|---|---|---|---|
| 1 | 390 | 3 | 41 | 17 |
| 2 | 390 | 3 | 49 | 25 |
| 3 | 390 | 3 | 53 | 34 |
| 4 | 390 | 3 | 56 | 28 |
| 5 | 390 | 3 | 58 | 28 |
| 6 | 390 | 3 | 45 | 24 |

What is claimed is:

1. A process for preparing an unsaturated carboxylic acid comprising subjecting an alkane, or a mixture of an alkane and an alkene, to vapor phase catalytic oxidation in the presence of a catalyst which comprises a mixed-metal oxide having the empirical formula $$Mo_aV_bE_cX_dO_e$$

wherein E is at least one element selected from the group consisting of Te and Sb, wherein X is at least one element selected from the group consisting of Nb, Ta, Ti, Al, Zr, Cr, Mn, Fe, Ru, Co, Rh, Ni, Pd, Pt, Ag, B, In, Ce and W, and wherein, when a=1, b=0.01 to 1.0, c=0.01 to 1.0, d=0.01 to 1.0 and e is dependent on the oxidation state of the other elements, and which is prepared by a process comprising:
(a) admixing compounds of Mo, V, E and X and at least one solvent to form a gel;
(b) aging said so-formed gel; and
(c) calcining said gel.

2. A process for preparing an unsaturated nitrile comprising subjecting an alkane, or a mixture of an alkane and an alkene, to vapor phase catalytic oxidation in the presence of ammonia and a catalyst which comprises a mixed-metal oxide having the empirical formula $$Mo_aV_bE_cX_dO_e$$

wherein E is at least one element selected from the group consisting of Te and Sb, wherein X is at least one element selected from the group consisting of Nb, Ta, Ti, Al, Zr, Cr, Mn, Fe, Ru, Co, Rh, Ni, Pd, Pt, Ag, B, In, Ce and W, and wherein, when a=1, b=0.01 to 1.0, c=0.01 to 1.0, d=0.01 to 1.0 and e is dependent on the oxidation state of the other elements, and which is prepared by a process comprising:
(a) admixing compounds of Mo, V, E and X and at least one solvent to form a gel;
(b) aping said so-formed gel; and
(c) calcining said gel.

* * * * *